(12) United States Patent
Hernandez

(10) Patent No.: US 9,632,016 B2
(45) Date of Patent: Apr. 25, 2017

(54) MATERIAL STRAIN MEASUREMENT METHOD BY MEANS OF LASER ABLATION

(71) Applicant: The Boeing Company, Chicago, IL (US)

(72) Inventor: Fernando E. Hernandez, Bothell, WA (US)

(73) Assignee: The Boeing Company, Chicago, IL (US)

( * ) Notice: Subject to any disclaimer, the term of this patent is extended or adjusted under 35 U.S.C. 154(b) by 634 days.

(21) Appl. No.: 13/897,621

(22) Filed: May 20, 2013

(65) Prior Publication Data

US 2014/0338461 A1 Nov. 20, 2014

(51) Int. Cl.

| | | |
|---|---|---|
| *F16B 31/02* | (2006.01) | |
| *G01N 29/14* | (2006.01) | |
| *G01H 5/00* | (2006.01) | |
| *G01N 3/22* | (2006.01) | |
| *B25B 23/14* | (2006.01) | |
| *G01L 5/24* | (2006.01) | |
| *B25B 23/142* | (2006.01) | |

(52) U.S. Cl.
CPC .............. *G01N 3/22* (2013.01); *B25B 23/14* (2013.01); *B25B 23/1425* (2013.01); *G01L 5/246* (2013.01)

(58) Field of Classification Search
CPC ...... B25B 23/14; B25B 23/1425; G01N 3/22; G01L 5/246
USPC .......................................................... 73/761
See application file for complete search history.

(56) References Cited

U.S. PATENT DOCUMENTS

| | | | |
|---|---|---|---|
| 4,294,122 A * | 10/1981 | Couchman | B25B 23/14 |
| | | | 411/14 |
| 4,569,229 A | 2/1986 | De Halleux | |
| 5,801,312 A | 9/1998 | Lorraine et al. | |
| 6,009,380 A | 12/1999 | Vecchio | |
| 6,837,109 B2 | 1/2005 | Okuno et al. | |
| 8,683,869 B2 * | 4/2014 | Herley | G01L 5/246 |
| | | | 73/760 |
| 2009/0031811 A1 | 2/2009 | Georgeson | |

OTHER PUBLICATIONS

Espacenet translation of abstract, JP2010008151, Hashiba Kunio, Jan. 2010.*
Yunis, Isam; Quinn, Roger D.; Kadambi, Jaidrishnan R.; The Practical Implementation of Non-Contacting Laser Strain Measuerment Systems; AIAA-200-1696, American Institute of Aeronautics and Astronautics, 2000.
Diaci, Janez; Mozina, Janez; On-line Optodynamic Monitoring of Laser Materials Processing; ISBN: 978-953-307-141-1, InTech, Available from: http://www.intechopen.com/books/advanced-knowledge-application-in-practice/on-lineoptodynamic- monitoring-of-laser-materials-processing.
Maran, J. and Kuhr, G.; "Acousto-optic Extensometer for Bolts"; NASA Tech Briefs, Summer 1984, p. 518.

* cited by examiner

*Primary Examiner* — Harshad R Patel
*Assistant Examiner* — Brandi Hopkins
(74) *Attorney, Agent, or Firm* — Felix L. Fischer

(57) ABSTRACT

A fastener strain measurement system employs a probe incorporating a laser emitter to provide a laser beam and an acoustic detection device. A system controller is configured to detect an acoustic wave resulting from the ablation created by the laser beam and calculate fastener strain based on the detected acoustic wave.

18 Claims, 6 Drawing Sheets

MATERIAL STRAIN MEASUREMENT METHOD BY MEANS OF LASER ABLATION

BACKGROUND INFORMATION

Field

Embodiments of the disclosure relate generally to the field of fastener installation and more particularly to a method and apparatus for direct measurement of fastener strain during tightening using laser ablation to create shockwaves within the fastener and detecting reflection of the shockwaves for preload measurement.

Background

Mechanical fasteners such as threaded bolts and associated nuts used in joining of structures for various applications including the manufacture of aircraft are typically installed using a torque value. Torque measurements may be adversely affected by variability in friction losses in the bolt and nut interaction as well as interaction with intermediate structural surfaces and sealants and lubricants employed in the assembly process. Existing torque tool systems, processes and specifications are becoming more expensive to maintain since all measurable data is dependent on a torque value not actual preload or strain measurement in the bolt.

It is therefore desirable to provide a method and apparatus for direct strain or preload measurement in fastener bolts.

SUMMARY

Embodiments disclosed herein provide a fastener strain measurement system employing a probe incorporating a laser emitter to provide a laser beam and an acoustic detection device. A system controller is configured to detect an acoustic wave resulting from ablation created by the laser beam and calculate fastener strain based on the detected acoustic wave.

The embodiments provide a method of measuring a fastener wherein a portion of a fastener is impinged for ablation with a laser beam from a laser emitter mounted in a probe. An acoustic wave responsive to the microscopic ablation is detected with a detector in the probe. A strain measurement of the fastener is then calculated based on data received by detecting the acoustic wave.

The features, functions, and advantages that have been discussed can be achieved independently in various embodiments of the present disclosure or may be combined in yet other embodiments further details of which can be seen with reference to the following description and drawings.

DETAILED DESCRIPTION

Embodiments disclosed herein provide an integrated system for strain measurement on a bolt for direct preload measurement. The strain measurement system employs a pulsed laser for controlled ablative impact on the bolt head with an acoustic detector, typically in the ultrasonic range, for measurement of a return signal resulting from the ablative impact. A control and display system provides direct output to an operator for measured strain in the bolt and conversion to a preload measurement for use in torqueing the bolt to a desired preload.

Figure 1:
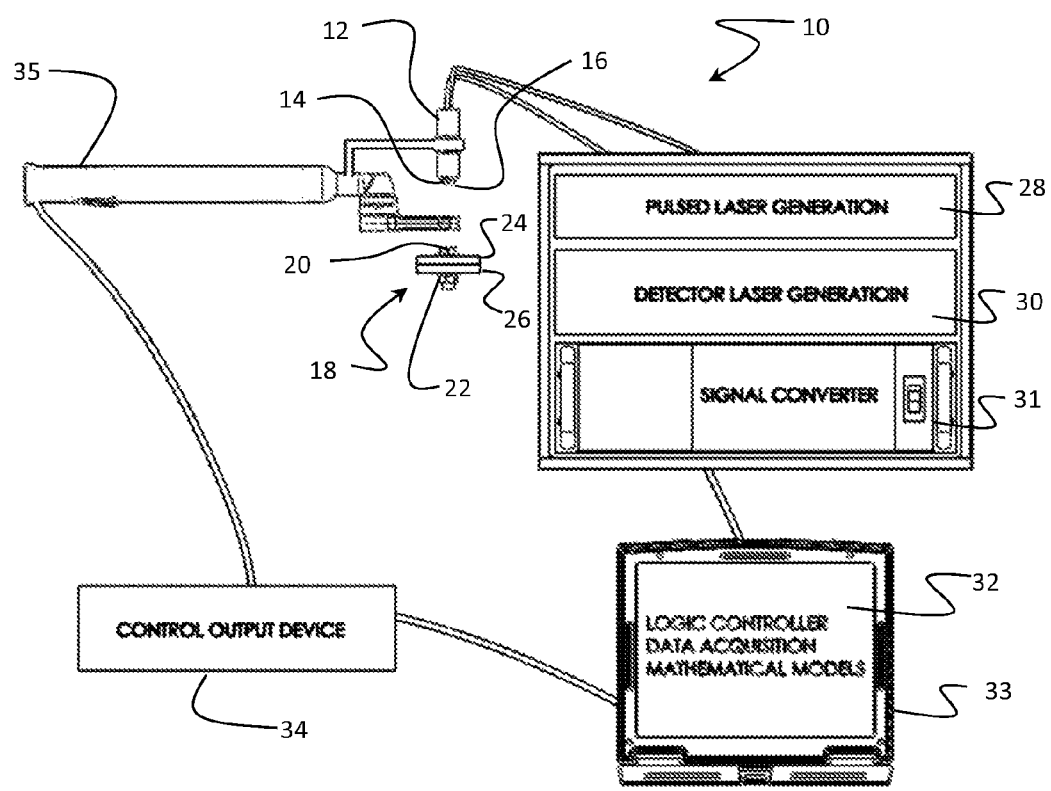
FIG. 1 is a schematic representation of an embodiment for the strain measurement system disclosed herein.

Referring to the drawings, FIG. 1 shows an exemplary embodiment of the strain measurement system 10 which incorporates an integrated probe 12 having a pulsed laser emitter 14 and a detector 16, both to be described in greater detail subsequently. The strain measurement system is adapted for use in measuring the strain or preload in a fastener system 18 which incorporates a bolt 20 and a nut 22 used to secure plates 24 and 26 or similar elements of a structural joint. A pulsed laser generation element 28 is connected to the probe with hardware and software control modules to power and control the pulsed laser emitter 14. A detector laser generation element 30 is connected to the probe with hardware and software control modules to generate a continuous wave laser source. A signal converter 31 is connected to the probe with hardware and software control modules to receive return signals representative of an acoustic return in the bolt 20 responsive to impingement of the pulsed laser on the bolt as will be described in greater detail subsequently. A display 32 associated with a system control computer 33 receives data from information transmitted by the detector 16 through the signal converter 31 and provides that data, computationally converted to direct strain measurement or preload, for use by an operator installing the fastener system 18. The system control computer 33 may also communicate with a control output device 34 associated with a fastener torqueing tool 35 on which the probe 12 may be mounted as described in greater detail subsequently.

Figure 2:
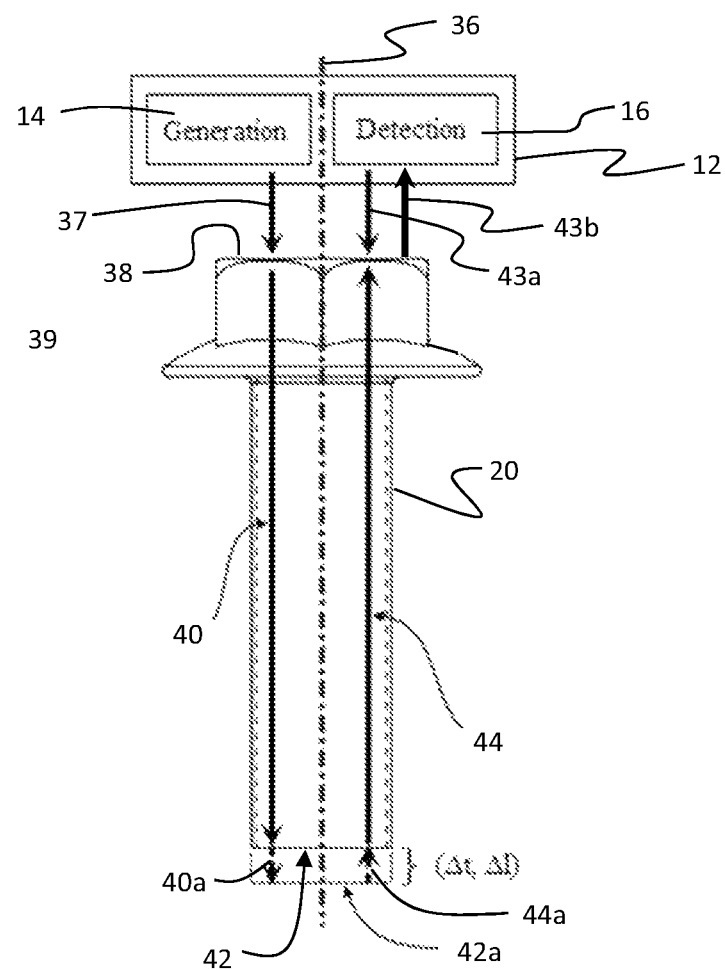
FIG. 2 is a schematic representation of the operation of the embodiment with an example bolt.

Physical operation of the probe 12 is depicted in FIG. 2. The probe 12 is substantially aligned with an axis 36 of the bolt 20. The pulsed laser emitter 14, such as a solid state Q-Switched ND:YAG or, in potential embodiments, a gas laser ($CO_2$ or Excimer), provides a laser beam 37 which impacts an upper surface 38 of a head 39 on the bolt 20. In an example embodiment employing a Q-switched Nd:YAG laser a wavelength of 1064 nm with pulse width of 10 ns is employed providing a pulse energy between 50 and 400 mJ. Sufficient power is provided in the pulsed laser beam to cause ablation of the upper surface 38 sufficient to impart a shock wave in the bolt 20. The ablative impact of the laser beam 37 on the bolt head upper surface 38 will generate a shockwave that translates into a longitudinal acoustic pulse 40 that travels through the bolt 20 and is reflected from an end surface 42 of the bolt as an acoustic reflection 44. As the acoustic reflection bounces back it hits the bolt head upper surface 38 causing a displacement proportional to the longitudinal wave amplitude. The acoustic reflection 42 is processed by the detector 16. For an exemplary embodiment, an acoustic detection device for the detector 14 is a continuous oscillation laser (Nd:YAG) with a wavelength of 532 nm providing a beam 43a and an associated photo detector and interferometer to detect a return beam 43b. The modulation of the return beam 43b, detected by the signal converter 31, will be representative of the acoustic reflection waves in bolt 20. In certain embodiments the photo detector may be present in the probe or connected through a fiber optic strand. Signal converter 31 employs high speed analog to digital (A/D) converters having a response time of at least 10 MHz. Enhanced resolution may be provided with A/D converters with 125 MHz to 1 GHz response. As represented in FIG. 2, torqueing of the bolt 20 results in extension of the end surface 42 from a relaxed position to a strained position 42a. This increase in length results in additional path length 40a for the acoustic pulse and additional path length 44a for the acoustic reflection which translates to time delay (Δt) proportional to the change in length (Δl) measurable by the detector 16.

Figure 3:
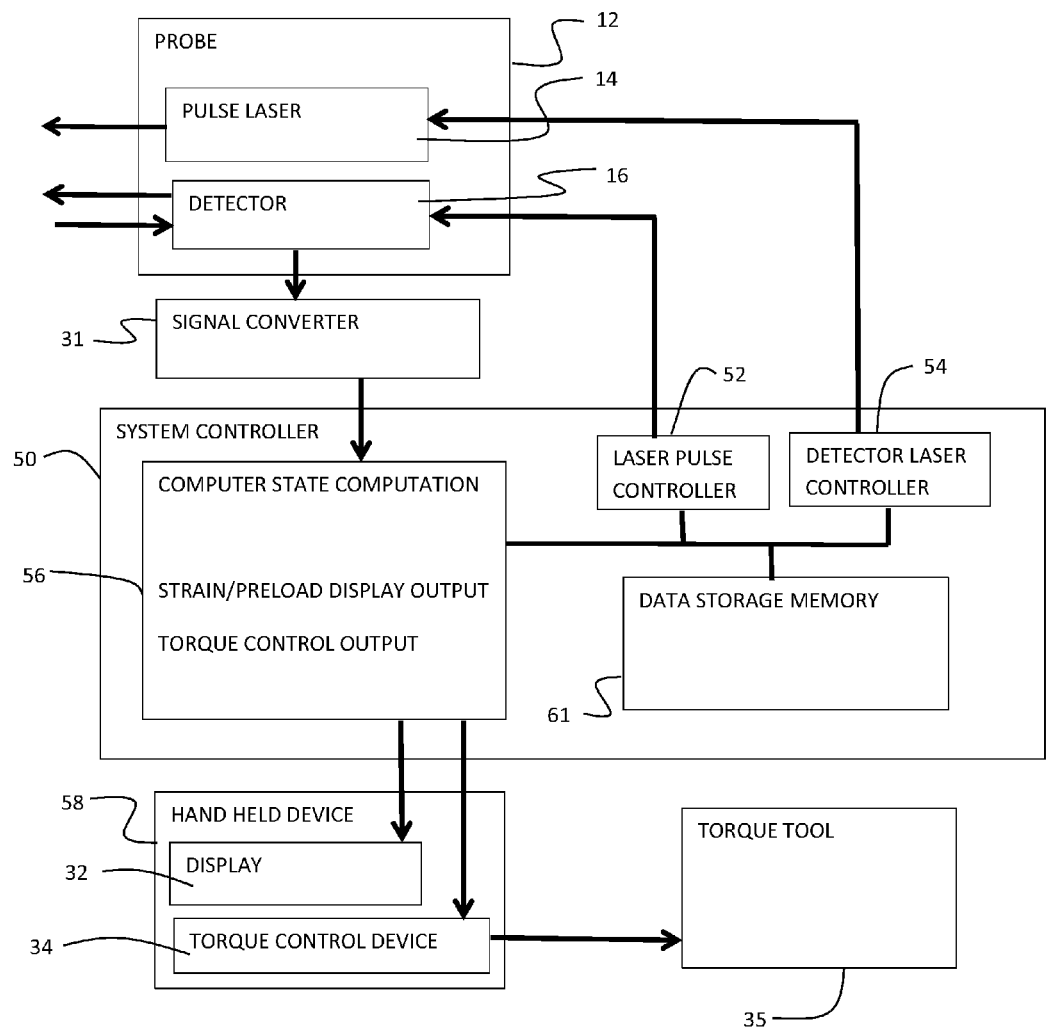
FIG. 3 is a block diagram of system control elements in the embodiment.

Overall control of the strain measurement system 12 is provided by a system controller 50 shown in FIG. 3, which may be microprocessor based or incorporated in a connected computer such as the system control computer 33 of FIG. 1 or similar device. The controller 50 interfaces with the laser generation element 28 with appropriate hardware and software modules to provide a laser pulse controller 52 for power and pulse timing control of the emitted laser beam. A detector laser controller 54 is incorporated to control the continuous wave laser in the detector 16. Pulse emission timing may also be provided from the laser pulse controller for use by a state computation engine 56. The state computation engine 56 incorporates appropriate hardware and software modules for processing of the detected acoustic reflection 42 received from the signal converter 31. The state computation engine 56, with appropriate filtering and resolution capability, compares return timing of the acoustic reflection through the modulated return beam 43b as detected by the signal converter 31 to determine a length of the bolt 20. The state computation engine 56 calculates a strain from the bolt length based on predetermined data for the fastener and comparison of bolt length in an untensioned or relaxed state. The state computation engine may then convert the calculated strain directly to a preload tension in the bolt 20. The strain and/or preload data may then be output on the display 32. In selected embodiments the display 32 or a secondary display may be provided on a hand held device 58 for use by the operator of the torqueing tool. Tool control output device 34 (shown in FIG. 1) may also be incorporated in the handheld device and incorporate control modules to issue a control signal to stop any torqueing action upon reaching a desired preload. The substantially continuous monitoring of the bolt strain by the continuous oscillation laser (Nd:YAG) beam 43a with associated photo detector and interferometer detecting return beam 43b and the signal converter 31 allows faster measurements and automated stopping of the torque tool (for example by disabling the operator's trigger based on the control signal) as the target preload is achieved. This avoids any overshoot preventing over tightening of the bolt. A memory 61 may be provided for use in computational processes by the state computation engine or other elements of the controller and for storage of results data.

Figure 4:
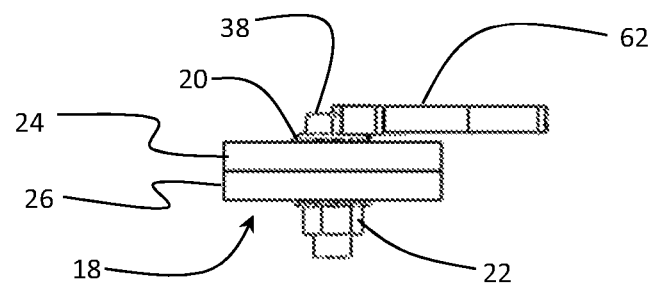
FIG. 4 is a prior art example of a wrench imparting torque on a bolt in a fastener.
Figure 5:
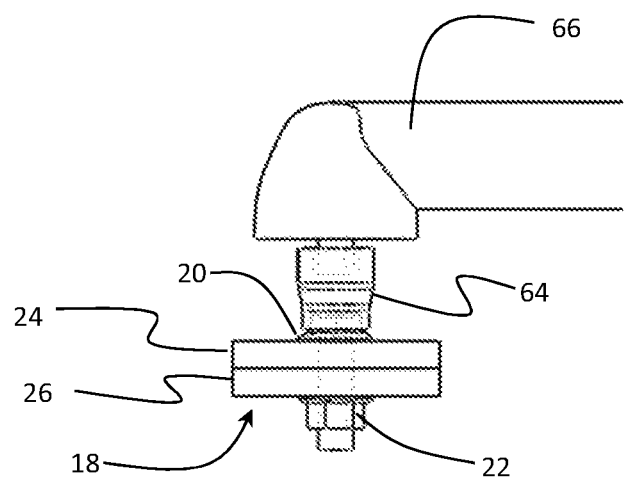
FIG. 5 is a side view of prior art example of a driving socket and ratchet or power tool for imparting torque on the bolt.
Figure 6:
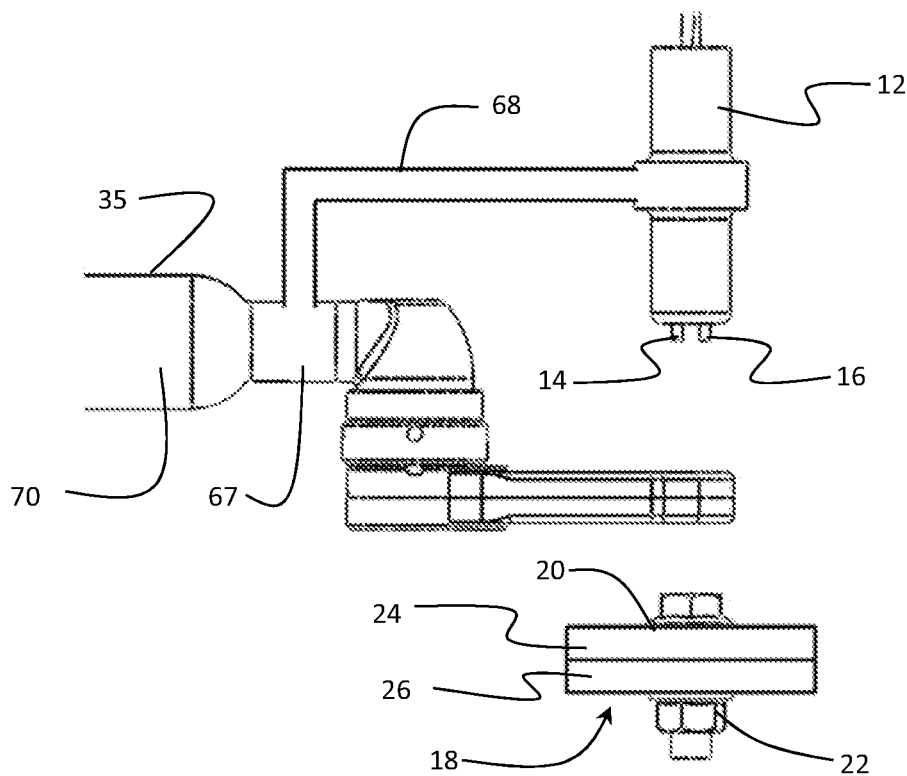
FIG. 6 is a side view of a wrench employing an integrated strain measurement system as defined herein.

FIG. 4 shows a fastener system torqueing arrangement with a wrench 62 engaging the head 38 of bolt 20 in the fastener system 18 for individual hand tightening of fasteners as known in the prior art. Similarly, FIG. 5 shows driving socket 64 engaging the head 38 of bolt 20 with a ratchet or power driven tool 66 applying axial rotation of the socket 64. Implementation of an embodiment of the strain measurement system, as previously disclosed, in conjunction with a wrench is shown in FIG. 6. The probe 12 is supported through a collar 67 by an articulating or rigid arm 68 extending from a handle 70 of the torque tool 35. The probe 12 is positioned over the bolt head for operation of the laser emitter 14 and detector 16 in the probe as previously described. Normal operation of the torque tool 35 by a technician torqueing the fastening system 18 may then be monitored by the probe in real time providing strain and/or preload data as the bolt 20 is tightened. In alternative embodiments, the arm 68 may separately support the probe from the structure in which the fastening system 18 is employed by means of a magnetic or suction cup attachment with the probe 12 axially positioned over the bolt 20. The probe 12 is then moved from bolt to bolt as fastener systems are torqued with the wrench 62.

Figure 7:
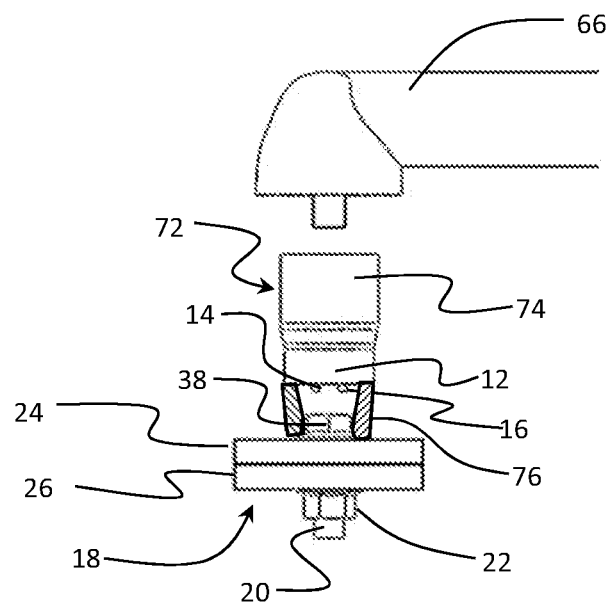
FIG. 7 is a side partial section view of a driving socket with an integral strain measurement system; and, FIG. 8 is a flow chart of a method for strain measurement employing an embodiment as disclosed herein.

An implementation of the embodiment with a socket arrangement is shown in FIG. 7. The probe 12 is integrated into a Laser Ultra Sound (LUS) socket 72 having an attachment hub 74 to receive the ratchet or power tool 66. A socket 76 extends from the probe 12 to engage the head 38 of bolt 20. The LUS socket maintains axial alignment of the probe 12 with the bolt head 38 and is directly moveable with the LUS socket 72 and power tool 66 as various fastener systems are torqued during assembly of a structure.

Figure 8:
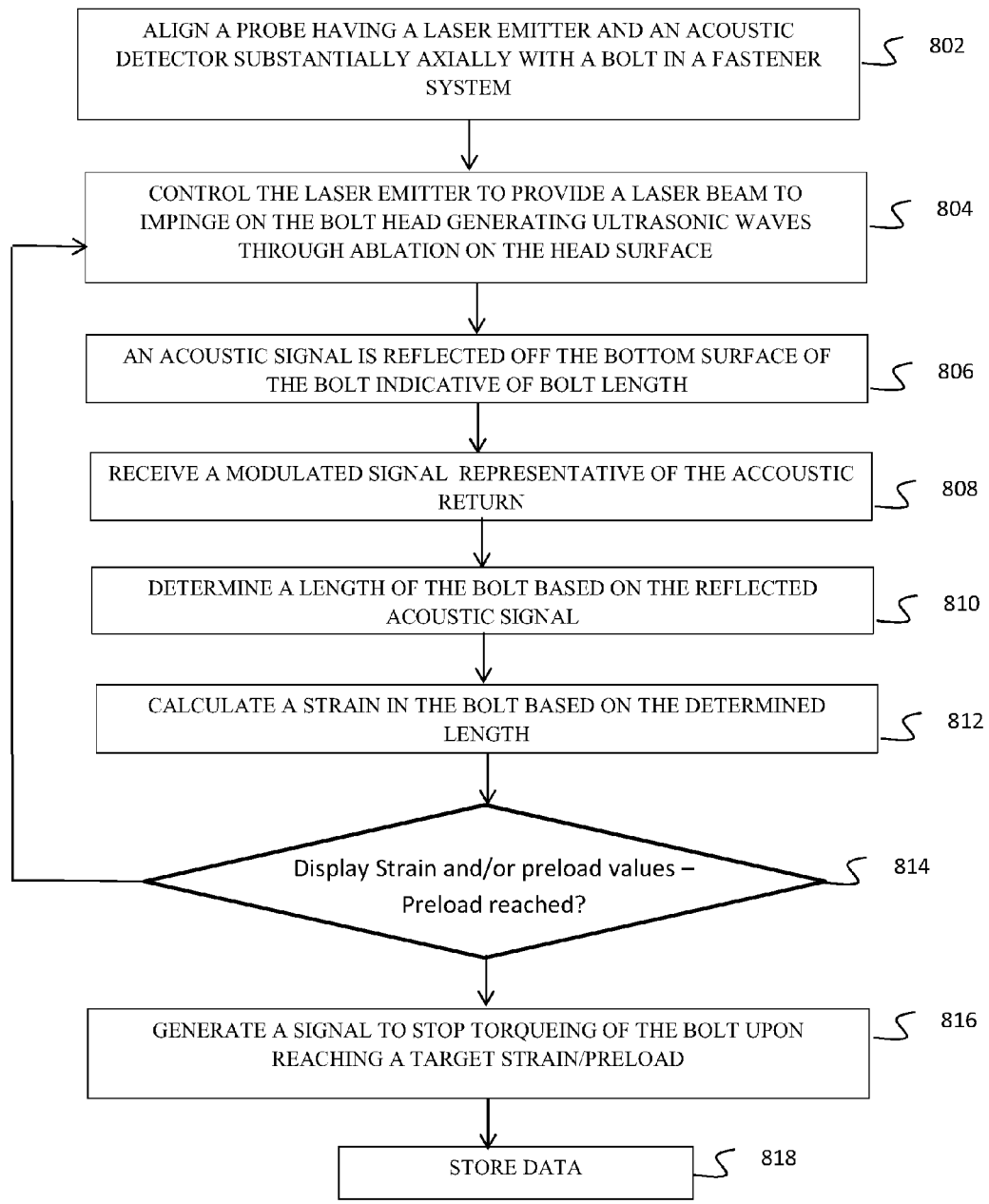

As shown in FIG. 8 the embodiments disclosed herein may be employed for direct strain or preload measurement by aligning a probe having a laser emitter and an acoustic detector substantially axially with a bolt in a fastener system, step 802. As previously described, the probe may be attached to a torque tool such as a wrench with an arm or integrated into an LUS for a socket and power tool torqueing application. The laser emitter is controlled to provide a laser beam to impinge on the bolt head, step 804, generating ultrasonic waves through ablation on the head surface of the bolt. An acoustic signal is reflected off the bottom surface of the bolt indicative of bolt length, step 805, and a modulated signal representative of the acoustic return is received by the detector, step 806. A length of the bolt may then be determined based on the reflected acoustic signal, step 808. A strain is then calculated in the bolt based on the determined length, step 810. The strain may be converted to a preload value, step 812, if desired and stress in the bolt may also be calculated. Strain, stress and/or preload values may then be displayed, step 814, and the ablation/measurement process continued until a predetermined preload is reached. Measurement of the strain may be accomplished as the bolt is being torqued and for automated systems, a signal may be generated to stop torqueing of the bolt upon reaching a target strain/preload, step 816, by sending a signal for on/off switch control on the torque tool. Data for records of the fastener system torqueing operation may then be stored for future reference or display, step 818.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. A fastener strain measurement system comprising:
 a fastening device configured to apply torque to a fastener;
 a probe supported in spaced relation from the fastening device, said probe incorporating
  a laser emitter providing a laser beam directed at a head of the fastener and providing a pulse energy between 50 and 400 mJ ablating material from the fastener head and inducing a longitudinal acoustic pulse and an acoustic detection device; and a system controller configured to compare return timing of an acoustic reflection of the longitudinal acoustic pulse, calculating a strain from a relaxed fastener length based on predetermined data for the fastener in an untensioned state and comparing the relaxed fastener length to a length determined by timing of the acoustic reflection, wherein said probe is configured to record the acoustic wave while the fastening device is applying a torque to the fastener.

2. The fastener strain measurement system as defined in claim 1 wherein the fastening device is a wrench.

3. The fastener strain measurement system as defined in claim 2 wherein the probe is supported by an arm for positioning the probe axially with respect to a fastener engaged by the wrench.

4. The fastener strain measurement system as defined in claim 3 wherein the arm is mounted to the wrench.

5. The fastener strain measurement system as defined in claim 1 wherein the fastening device is a socket driven by a ratchet or power driven tool.

6. The fastener strain measurement system as defined in claim 5 wherein the probe is integrated with the socket in a Laser Ultra Sound (LUS) socket.

7. The fastener strain measurement system as defined in claim 1 wherein the laser emitter is selected from the set of a solid state Q-Switched ND:YAG or gas laser.

8. The fastener strain measurement system as defined in claim 1 wherein the system controller incorporates
- a laser pulse controller connected to the laser emitter for control of laser pulsing;
- an acoustic processor receiving data from the acoustic detection device for determination of the acoustic reflection which translates to time delay proportional to a tensioned length of the fastener based on the detected acoustic wave; and,
- a state computation device receiving the change in length from the acoustic processor and calculating the strain from a relaxed fastener length and comparing the relaxed fastener length to the tensioned length determined by timing of the acoustic reflection.

9. The fastener strain measurement system as defined in claim 8 further comprising a display receiving the strain for display to an operator.

10. The fastener strain measurement system as defined in claim 9 wherein the state computation device further computes a preload tension value based on the strain and the display further receives the preload tension value for display to the operator.

11. The fastener strain measurement system as defined in claim 10 further comprising a memory in the system controller for storing strain and preload tension values for torqued fastener systems.

12. A method of measuring a fastener comprising:
connecting a probe to a torqueing tool;
employing the torqueing tool for tightening of a fastener;
impinging a portion of the fastener with a laser beam from a laser emitter mounted in the probe and providing a pulse energy between 50 and 400 mJ to ablate material from the fastener head inducing a longitudinal acoustic pulse;
detecting an acoustic reflection responsive to the longitudinal acoustic pulse with an acoustic detector in the probe; and,
calculating a strain measurement of the fastener based on data received by comparing return timing of the acoustic reflection of the acoustic pulse, calculating a strain from a relaxed fastener length based on predetermined data for the fastener in an untensioned state and comparing the relaxed fastener length to a length determined by timing of the acoustic reflection.

13. The method of claim 12 further comprising aligning the probe substantially axially with a bolt in the fastener.

14. The method of claim 12 wherein the torqueing tool is a wrench and further comprising attaching the probe to the wrench with an arm.

15. The method of claim 12 wherein the torqueing tool is a socket with a ratchet or power driven tool and further comprising integrating the probe into an LUS with the socket.

16. The method of claim 12 wherein the step of detecting an acoustic wave includes receiving a reflected acoustic wave.

17. The method of claim 16 wherein the step of calculating a strain measurement further comprises determining a length of a bolt in the fastener from the reflected acoustic wave and calculating strain based on the length and further comprising calculating preload tension in the bolt based on the strain.

18. The method of claim 17 further comprising displaying the strain or preload tension data during torqueing of the fastener.

* * * * *